(12) United States Patent
Fernfors

(10) Patent No.: US 7,347,848 B2
(45) Date of Patent: Mar. 25, 2008

(54) ABSORBENT ARTICLE AND METHOD FOR ITS MANUFACTURE

(75) Inventor: Ingemar Fernfors, Mölndal (SE)

(73) Assignee: SCA Hygiene Products AB, Gothenburg (SE)

( * ) Notice: Subject to any disclaimer, the term of this patent is extended or adjusted under 35 U.S.C. 154(b) by 322 days.

(21) Appl. No.: 10/145,884

(22) Filed: May 16, 2002

(65) Prior Publication Data

US 2002/0193776 A1 Dec. 19, 2002

Related U.S. Application Data

(60) Provisional application No. 60/290,951, filed on May 16, 2001.

(30) Foreign Application Priority Data

May 16, 2001 (SE) .................................... 0101731

(51) Int. Cl.
*A61F 13/15* (2006.01)
(52) U.S. Cl. ........................ 604/392; 604/386
(58) Field of Classification Search ........ 604/386–387, 604/391–392, 393–394
See application file for complete search history.

(56) References Cited

U.S. PATENT DOCUMENTS

| | | | | |
|---|---|---|---|---|
| 4,909,802 A | * | 3/1990 | Ahr et al. | 604/385.3 |
| 5,549,593 A | * | 8/1996 | Ygge et al. | 604/391 |
| 5,624,428 A | * | 4/1997 | Sauer | 604/391 |
| 5,662,636 A | | 9/1997 | Benjamin et al. | |
| 5,685,873 A | * | 11/1997 | Bruemmer | 604/385.24 |
| 5,695,488 A | * | 12/1997 | Sosalla | 604/385.24 |
| 5,870,778 A | * | 2/1999 | Tharpe | 2/400 |
| 6,110,157 A | | 8/2000 | Schmidt | |
| 6,730,070 B2 | * | 5/2004 | Holmquist | 604/392 |

FOREIGN PATENT DOCUMENTS

| | | |
|---|---|---|
| EP | 0 485 691 A2 | 5/1992 |
| EP | 0 611 607 A1 | 8/1994 |
| SE | 514 370 C2 | 4/1999 |
| WO | 91/08725 A1 | 6/1991 |
| WO | 99/21522 | 5/1999 |
| WO | 99/37263 | 7/1999 |
| WO | 00/27330 | 5/2000 |
| WO | 02/26183 A1 | 4/2002 |

\* cited by examiner

*Primary Examiner*—Tatyana Zalukaeva
*Assistant Examiner*—C. Lynne Anderson
(74) *Attorney, Agent, or Firm*—Buchanan Ingersoll & Rooney PC

(57) ABSTRACT

An absorbent article is provided with a belt 9, 9' attached to or adapted to be attached to the back portion 6 of the article and to the front portion 5 of the article in such a way that the article assumes a pantlike shape, where the belt forms part of the waist portion of the pant and has an outside 11, 11' and an inside 12, 12' which is intended to be in direct contact with a user. The belt comprises first 9 and second 9' belt halves which at one of their ends are permanently attached to the topsheet within bonding areas 13, 13' of the insides 12, 12' in such a way that the belt halves 9, 9' remain substantially flat along their entire length when brought against the topsheet on top of each other, and in such a way that joints 14, 14' which are formed at the bonding areas will be pressed outwards in directions away from the user when the absorbent article is used.

11 Claims, 4 Drawing Sheets

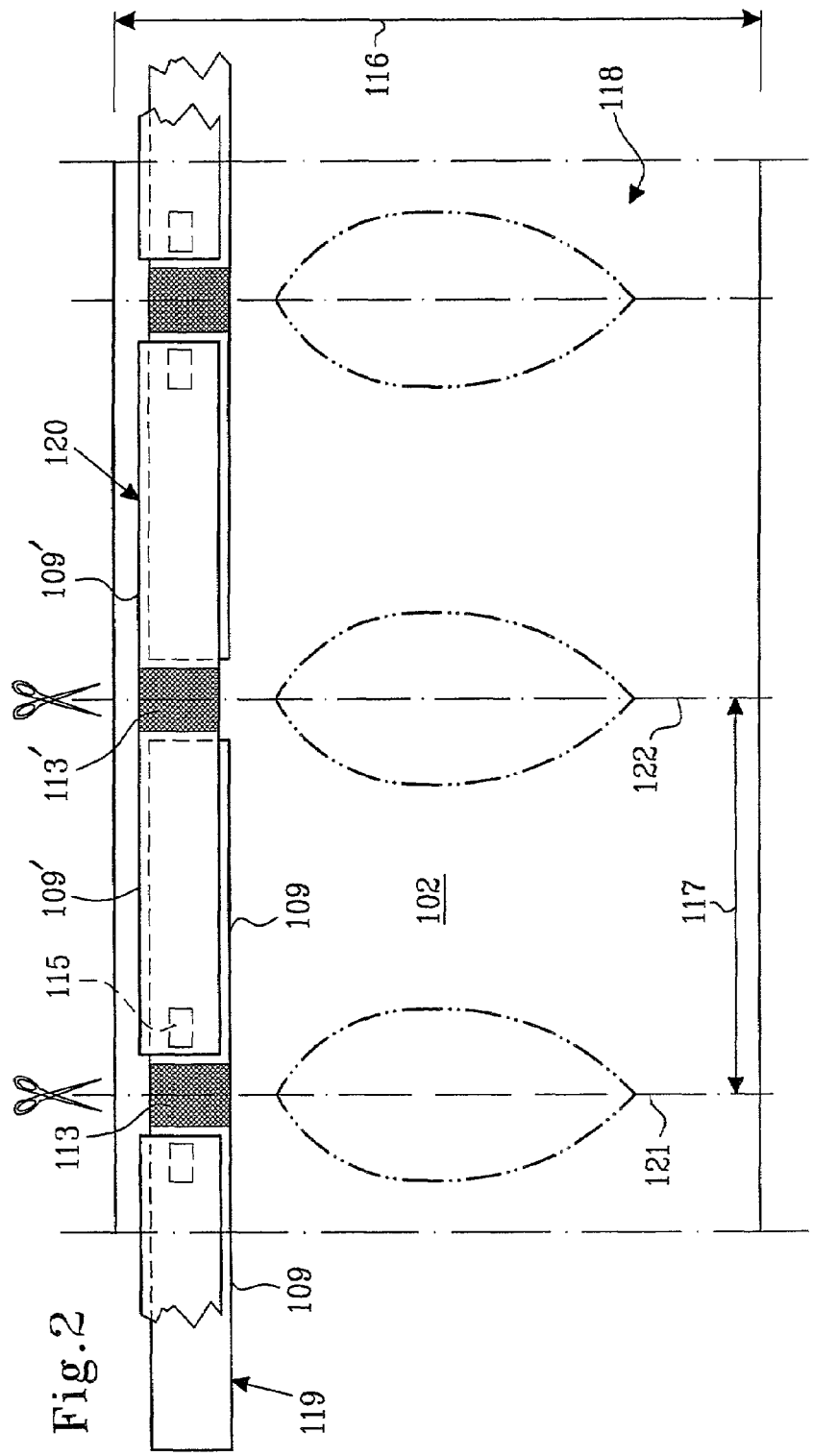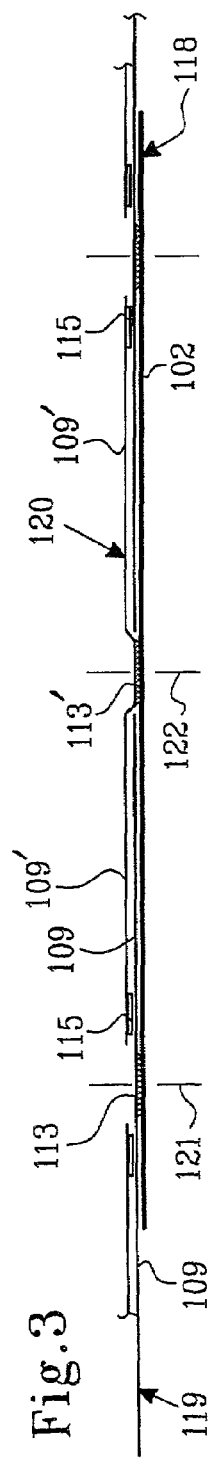

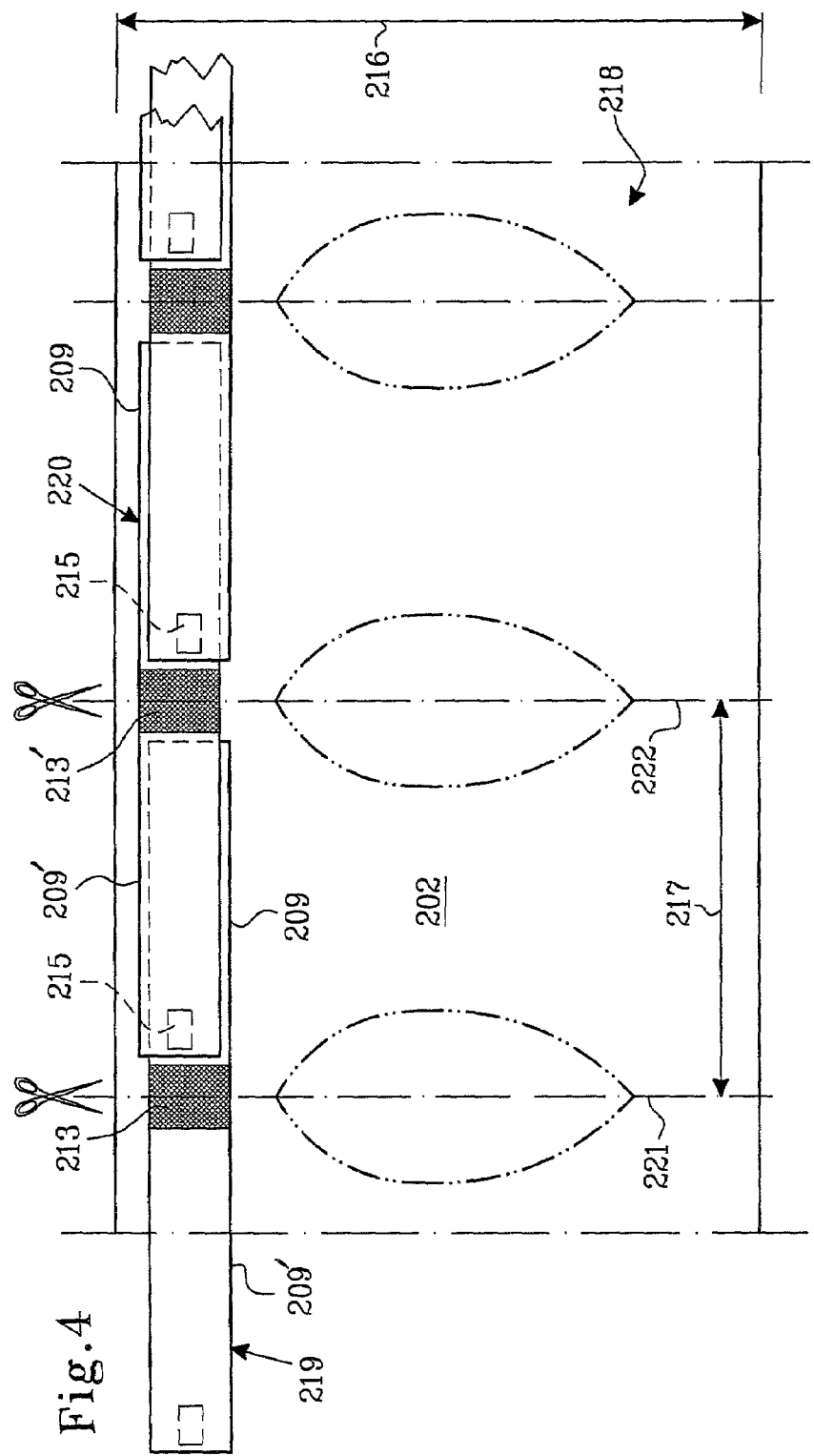
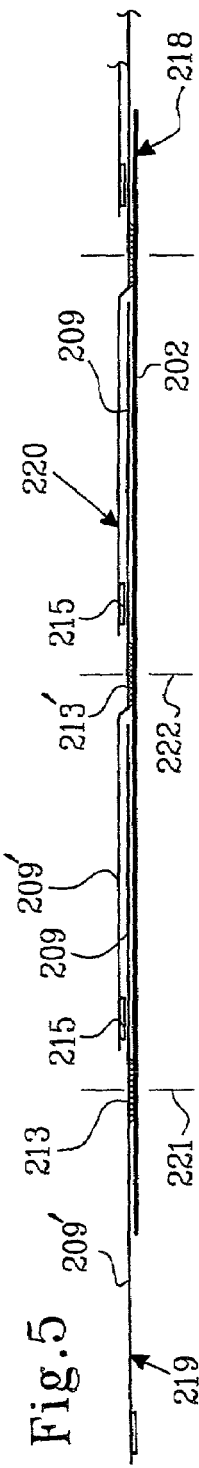
Fig.4
Fig.5

ABSORBENT ARTICLE AND METHOD FOR ITS MANUFACTURE

CROSS-REFERENCE TO RELATED APPLICATIONS

The present application claims the priority of U.S. Provisional Patent Application No. 60/290,951, filed May 16, 2001, and Swedish Patent Application No. 0101731-8, filed on May 16, 2001, the subject matter of which is hereby incorporated herein by reference.

TECHNICAL FIELD

The present invention relates to an absorbent article, such as a diaper or an incontinence guard, which is provided with a belt. The invention further relates to a method for manufacturing such an absorbent article.

BACKGROUND OF THE INVENTION

Absorbent articles, such as disposable diapers for infants or adults, are usually provided with a fastening system comprising a pair of fastening tabs attached to end portions of the article. As a rule, an absorbent article is applied to a user who is lying down. The fastening tabs are intended to engage receiving members located on the other end portion of the article. Such a fastening system is satisfactory when, e.g., diapers are applied to an infant, but problems may arise when an incontinence diaper is to be applied to an adult user, particularly in case the user wants to put the diaper on by himself/herself.

It has been found that absorbent articles provided with a belt, so-called belt diapers, are easier to put on a user who is standing up. Belted absorbent garments are disclosed, for example, in the international patent application No. PCT/SE99/01975 and in Swedish patent No. 514 370.

Furthermore, the international patent application No. WO 99/37263 discloses a method and an apparatus for manufacturing belted garments, such as belt diapers, which comprise a first belt half and a second belt half which both have a longitudinal extension. A carrier web on which the first and second belt halves are to be fixed has a first surface and a second surface.

The method according to WO 99/37263 comprises the step of placing the first belt half and the second belt half in a partially overlapping relationship so that a first end region of the first belt half and a first end region of the second belt half contact each other within a region of overlap, wherein a second end region of the first belt half and a second end region of the second belt half remain uncovered. The method further comprises the steps of releasably joining the first end regions of the first and second belt halves in order to create a temporary laminate, to bring the first surface of the carrier web and the temporary laminate in mutual contact so that the first surface of the carrier web contacts the laminate in the region of overlap of the first end regions of the belt halves, and to get at least a portion of the second end region of the first belt half and at least a portion of the second end region of the second belt half to contact the second surface of the carrier web.

Even if the previously known diapers and absorbent garments provided with belts have solved some of the above-mentioned problems with difficult application, there is still room for improvements.

Absorbent articles and garments according to the prior art, for instance, sometimes may be perceived as uncomfortable by a user, primarily because of the presence of protruding joints and material edges which are pressed directly against the skin when applying the belt of the article. Where comfort is concerned, it would therefore be a major advantage to be able to provide an absorbent article or garment having a belt where no such edges pressed inwards against the waist of the user will occur beneath the belt when the article has been put on.

Furthermore, the application of belts on absorbent articles during their production has usually been complicated with a large number of different process steps, intermediate laminates, etc. In some cases, this has resulted in runnability problems and a low production rate. For this reason, there is a need for a simple and production efficient method for furnishing an absorbent article or garment with a belt.

SUMMARY OF THE INVENTION

Accordingly, a first object of the present invention is to provide an absorbent article having a belt which eliminates the above-mentioned problem with inwardly-protruding joints and material edges which may be pressed against the skin of a user, and which article ensures that the user can wear the article with the highest possible degree of comfort.

This first object is achieved by means of an absorbent article, such as a diaper or an incontinence guard, which article comprises a liquid-pervious topsheet, a substantially liquid-impermeable backsheet and an absorbent body enclosed therebetween, and which has a front portion, a back portion and a crotch portion therebetween, and which further is provided with a belt attached to or intended to be attached to the back portion of the article and to the front portion of the article in such a way that the article assumes a pantlike shape where the belt forms part of the waist portion of the pant and has an outside and an inside which is intended to be in direct contact with a user. According to the invention, the belt comprises first and second belt halves which at one of their ends are permanently attached to the topsheet within bonding areas of the insides in such a way that the belt halves remain substantially flat along their entire length when being brought against the topsheet on top of each other, and in such a way that joints created at the bonding areas will be pressed outwards in directions away from the user when the absorbent article is used.

A second object of the present invention is to provide a simple and production efficient method for manufacturing the absorbent article according to the invention.

This second object is achieved by means of a method for manufacturing an absorbent article, such as a diaper or an incontinence guard, comprising a liquid-pervious topsheet, a substantially liquid-impermeable backsheet and an absorbent body enclosed therebetween, and which has a front portion, a back portion and a crotch portion therebetween, and which further is provided with a belt attached to or intended to be attached to the back portion of the article and to the front portion of the article in such a way that the article assumes a pantlike shape where the belt forms part of the waist portion of the pant and has an outside and an inside which is intended to be in direct contact with a user. According to the invention, the method thereby comprises permanently attaching first and second belt halves at one of their ends to the topsheet within bonding areas of the insides in such a way that the belt halves remain substantially flat along their entire length when being brought against the topsheet on top of each other, and in such a way that joints created at the bonding areas will be pressed outwards in directions away from the user when the absorbent article is used.

Further objects of the present invention will become evident from the following description, and the features enabling these further objects to be achieved are listed in the dependent claims.

BRIEF DESCRIPTION OF THE DRAWINGS

In the following, the invention will be described in greater detail with reference to the attached drawings, in which FIG. 1 schematically and with a cut-away portion shows an absorbent article according to a preferred embodiment of the invention, FIG. 2 schematically illustrates a method according to a first, particularly preferred embodiment of the invention which is intended for transversal production, FIG. 3 is section through the upper, longitudinal edge portion of the web 118 in FIG. 2, FIG. 4 schematically illustrates a method according to a second, advantageous embodiment of the invention, which also is intended for transversal production, FIG. 5 is a section through the upper, longitudinal edge portion of the web 218 in FIG. 4, and FIG. 6 schematically illustrates a method according to an alternative embodiment of the invention, which is intended for longitudinal production.

DETAILED DESCRIPTION OF THE PREFERRED EMBODIMENTS

Figure 1:
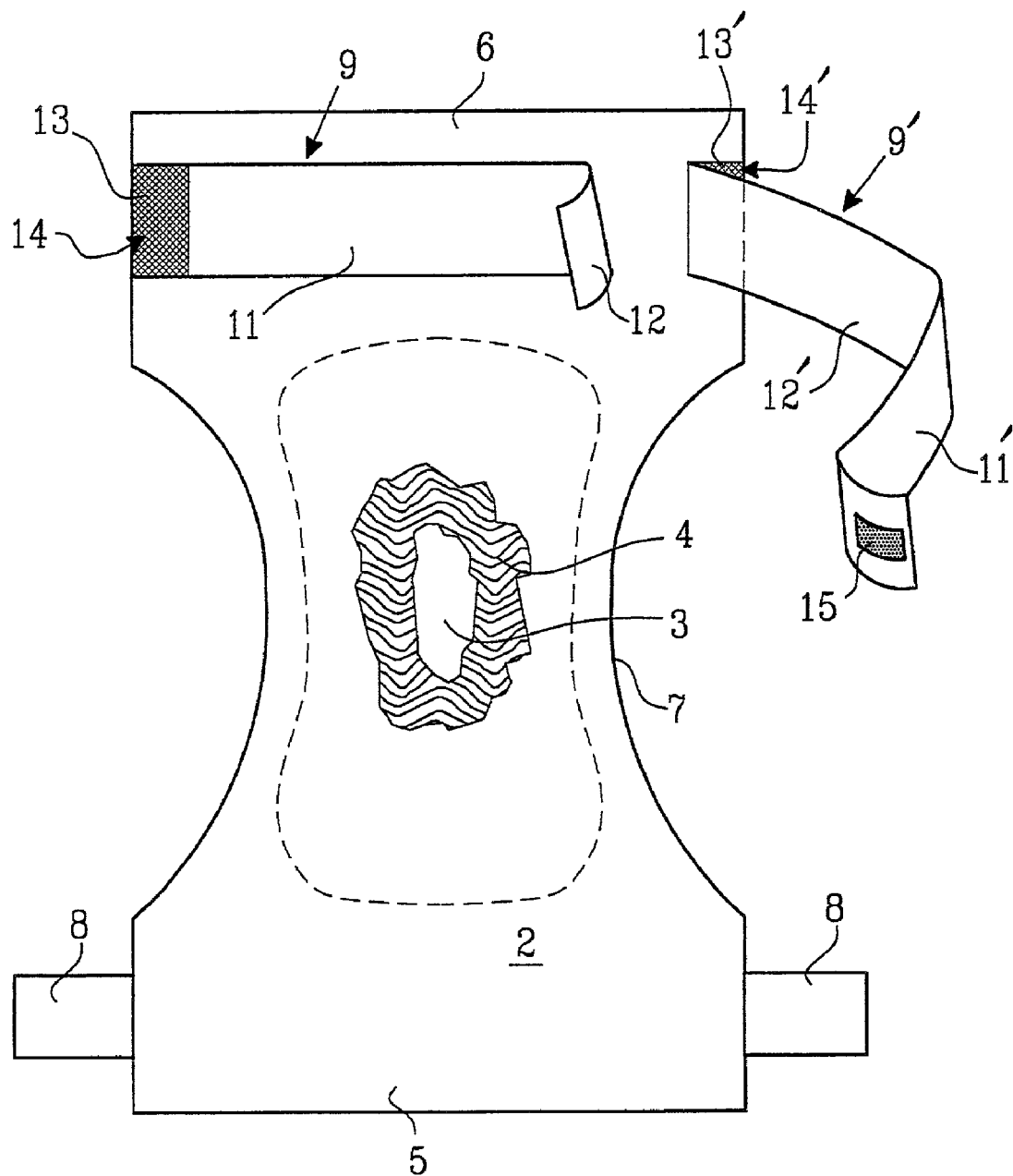

FIG. 1 schematically shows an absorbent article according to a preferred embodiment of the invention, more specifically a belt diaper intended for adults who suffer from incontinence. However, the invention is not limited to adult diapers, and absorbent articles or garments according to the invention which are intended to be used by young persons or infants are also conceivable.

The absorbent article 1 comprises a liquid-pervious topsheet 2, a substantially liquid-impermeable backsheet 3 and an absorbent body enclosed therebetween. The liquid-pervious topsheet 2 can consist of a nonwoven material, e.g., a spunbond material of continuous filaments, a meltblown material, a bonded carded fiber material, or another soft, flexible and liquid-pervious material. The substantially liquid-impermeable backsheet 3 can consist of a plastic film, a nonwoven material coated with a liquid-impermeable material, a hydrophobic nonwoven material, or another flexible material which resists liquid penetration.

The topsheet 2 and the backsheet 3 have a somewhat larger extension in the plane than the absorbent body 4 and extend beyond the edges thereof. The layers 2 and 3 are attached to each other within their projecting portions, e.g. by means of gluing or welding by means of heat or ultrasonics.

The absorbent body 4 can be of any conventional type. Examples of commonly occurring absorption materials are cellulosic fluff pulp, tissue layers, highly absorbent polymers (so-called superabsorbents), absorbent foam materials, absorbent nonwoven materials, and the like. It is common to combine cellulosic fluff pulp with superabsorbents in an absorbent body. It is also common with absorbent bodies comprising layers of different materials having different properties when liquid acquisition ability, distribution ability, and storage capacity are concerned. This is well known to the skilled person and will therefore not be described in detail. The absorbent body is preferably, but not necessarily, of the relatively thin type which is nowadays common for example in baby diapers and certain types of incontinence guards, and which comprises a compressed, blended or layered structure of cellulosic fluff pulp and superabsorbent.

The diaper 1 is intended to enclose the lower portion of the trunk of the wearer as a pair of absorbent pants. It comprises a front portion 5 which, during use, is intended to be worn against the front of the body of the user, a back portion 6, which during use, is intended to be worn against the back of the body of the user, and between the front and back portions a narrower crotch portion 7 which, during use, is intended to be located in the crotch area between the legs of the user. The front portion 5 is advantageously provided with a pair of adhesive tape tabs or other suitable fastening members, and preferably with hook members 8 belonging to a fastening element of the type which is often referred to as hookand-loop fastening means or "Velcro" closing.

The article is further provided with a belt 9, 9' attached to or intended to be attached to the back portion 6 of the article and to the front portion 5 of the article in such a way that the article assumes the pantlike shape. Thereby, the belt 9, 9' will form part of the waist portion of the pant and has an outside 11, 11' and an inside 12, 12' which is intended to be in direct contact with the user.

In the absorbent article 1 according to the invention, the belt comprises first 9 and second 9' belt halves which at one of their ends are permanently attached to the topsheet 2 within bonding areas 13, 13' of the belt insides 12, 12'. According to the invention, the belt halves 9, 9' are attached in such a way that they remain substantially flat along their entire length when being brought against the topsheet on top of each other, and in such a way that joints 14,14' which are created at the bonding areas will be pressed outwards in directions away from the user when the absorbent article is used. That is, within each bonding area 13 (or 13') the outside 11 (or 11') of the belt half is spaced farther from the backsheet 3 than is the inside 12 (or 12'). i.e., it is spaced farther by a distance equal to the thickness of the belt.

For example, the joint 14' between the second belt half 9' and the remaining absorbent article 1 according to the invention will not exhibit any material edge whatsoever during use protruding or extending inwards towards the waist of the user, and which could be pressed against the skin of the user and irritate this. According to this embodiment, the joint instead will be formed by means of joining two material layers on top of each other at a common end portion, after which the layers are folded away from each other and the joined portion will assume a "raised" position where the joint 14' strives outwards and away from the user. As such, the joint is located at a position outside of the belt so that an uninterrupted portion of the belt is arranged between the user and the joint, and an inside surface of the belt faces the user during use of the article. Alternatively, the raised joint is folded down against one of the material layers and is laid in parallel therewith, so that a substantially smooth surface facing inwards towards the user is obtained. This also applies to the corresponding joint 14 of the first belt half 9 or part. Accordingly, the joints 14, 14' or attachment areas where the belt halves 9, 9' are attached to the topsheet 2 of the absorbent article 1 according to the invention will exhibit a very low contact pressure or even no contact at all with the skin of the user. This is rather remarkable, since a conventional belt diaper would cause a higher contact pressure against the skin of the user at the belt attachment areas than along the remaining waistband of the pantlike shape. The low or nonexistent contact pressure against the waist of the user which is obtained at the belt attachment areas or joints 14, 14' ensures that the user can wear the absorbent article with the highest possible degree of comfort.

In an alternative embodiment of the absorbent article according to the invention, pieces of reinforcement material (only shown in FIG. 6) are permanently attached to opposite edge portions of the topsheet, wherein the insides of one end of the belt halves within bonding areas are attached to the topsheet via the pieces of reinforcement material. Also in this embodiment, no material edges extending inwards and which could exert a pressure which locally is too high against the skin of the user will be created at the belt attachment areas. Advantageously, the pieces of reinforcement material comprise an elastic material, something which gives the user of the absorbent article an improved comfort.

In addition to the fact that the absorbent article gives a very low or no contact pressure against the skin of the user at the attachment areas of the belt halves, the two-parted belt design does not give any risk of a contact pressure against the skin of the user which is too high occurring locally against the back of the user. The reason for this is of course that no material edges which could be pressed inwards against the back of the user are present, since the belt halves do not continue around the waist on the back side of the user.

The belt halves 9, 9 can be attached to the topsheet 2 within the bonding areas 13, 13' by means of any suitable method, by means of gluing or advantageously by means of thermal bonding with heat, but preferably by means of thermal bonding with ultrasonics. The belt halves are with their opposite ends intended to be possible to fasten together during use, e.g., by means of a tape tab, and preferably by means of a hook-and-loop fastening means. Particularly advantageously, a hook member 15 of a hook-and-loop fastening means can be provided on one of the insides 12' of the belt halves 9', wherein the outside 11 of the other belt half 9 provides a loop material interacting with the hook member. Alternatively, a hook member can be provided on the outside of one of the belt halves, and a loop material on the inside of the other belt half.

The above-discussed fastening members 8 or corresponding fastening members on the front portion 5 are intended to be attached against the outside 11, 11' of the belt halves 9, 9' in order to fasten together the diaper into the desired pantlike shape. The fastening members 8 preferably are hook members, but can also be of another suitable type.

The belt halves 9, 9' can consist of any material which is suitable for the purpose and, for example, can consist of a laminate consisting of an outside material 11, 11' forming the outside of the belt and a particularly soft nonwoven material 12, 12', which forms the inside of the belt and is intended to be in direct contact with the skin of the user. In such a laminate, the outside material for example can be a plastic film, and the inside material a spunbond material of polypropylene or polyethylene with a low bonding degree. In the preferred embodiment, where the outside material and/or the inside material should function as a loop material, the outside and/or the inside of the belt should of course consist of or comprise portions of a material which is able to interact with the hook members of the fastening system.

FIGS. 2 and 3 schematically illustrate a method according to a preferred embodiment of the invention which is intended for transversal production of absorbent articles. In this context, transversal production means that the production takes place with the absorbent articles arranged sidewise in the machine direction of the diaper machine.

The method is intended for manufacturing an absorbent article (see FIG. 1), such as a diaper or an incontinence guard, comprising a liquid-pervious topsheet 2, a substantially liquid-impermeable backsheet 3 and an absorbent body 4 enclosed therebetween. The absorbent article has a front portion 5, a back portion 6 and a crotch portion 7 therebetween, and is further provided with a belt 9, 9' attached to or intended to be attached to the back portion 6 of the article and to the front portion 5 of the article in such a way that the article assumes a pantlike shape, where the belt forms part of the waist portion of the pant and has an outside 11, 11' and an inside 12, 12' which is intended to be in direct contact with a user.

The method comprises permanently attaching first 9 and second 9' belt halves at one of their ends to said topsheet 2 within bonding areas 13, 13' of said insides 12, 12' in such a way that the belt halves 9, 9' remain substantially flat along their entire length when being brought against the topsheet on top of each other, and in such a way that joints 14, 14' formed at the bonding areas will be pressed outwards in directions away from said user when the absorbent article is used.

In the preferred embodiment of the method according to the invention, the absorbent article has an article length 116; 216 and an article width 117; 217, and several of the topsheets 102; 202 are provided in the form of a carrier web 118; 218.

In this manner, a first web 119; 219 is bonded to the carrier web 118; 218 within a first bonding area 113; 213 at a first end of the article width 117; 217, whereas a second web 120; 220 displaced by one article width 117; 217 and placed partially on top of the first web 119; 219 is bonded to the carrier web within a second bonding area 113'; 213' at a second, opposite end of the article width. Thereafter, the first web and the carrier web are cut along a first line 121; 221 dividing the first bonding area 113; 213, whereas the second web and the carrier web are cut along a second line 122; 222 dividing the second bonding area 113'; 213 in order to give the absorbent article the belt 109, 109'; 209, 209'.

In a preferred embodiment of the method according to the invention, the first 119; 219 and second 120; 220 webs are both shorter than two times the article width 117; 217. However, within the scope of the invention, it is conceivable to have embodiments where the first and second webs have a larger length than two times the article width, for example an embodiment where one or both of the free ends of the belt halves are doubled.

In the preferred embodiment illustrated in FIGS. 2 and 3, the first web 119 comprises two of the first belt halves 109, whereas the second web 120 comprises two of the second belt halves 109'. Alternatively, the first web can comprise two of the second belt halves, and the second web two of the first belt halves.

In a second, advantageous embodiment of the method according to the invention, particularly illustrated in FIGS. 4 and 5, both the first 219 and the second 220 webs comprise one of the first belt halves 209 and one of the second belt halves 209'.

Figure 6:
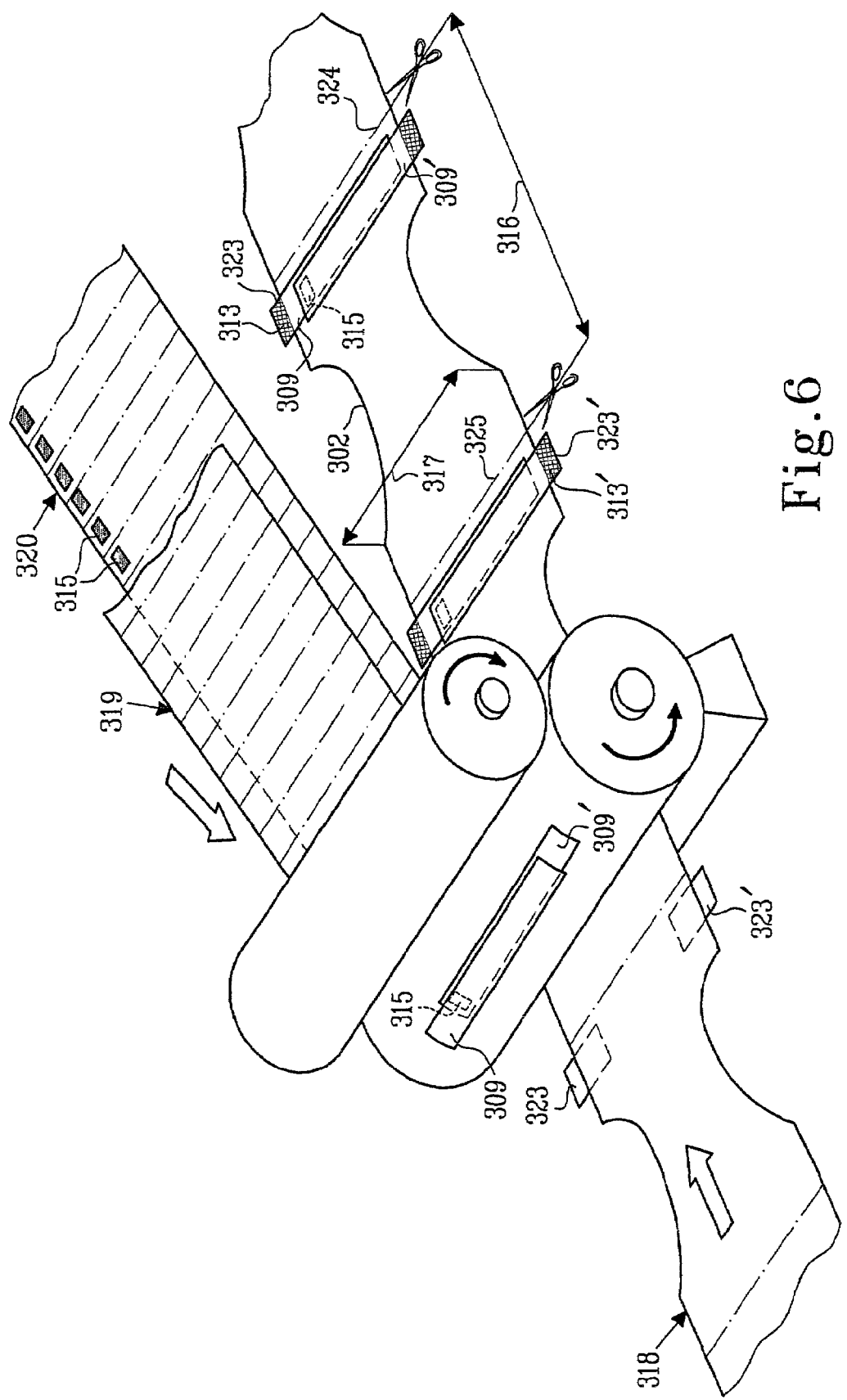

FIG. 6 is a schematic illustration of a method according to an alternative embodiment of the invention which is intended for longitudinal production, i.e., the length direction of the absorbent articles moves in the machine direction of the diaper machine during production.

In the alternative embodiment of the method according to the invention, the absorbent article has an article length 316 and an article width 317, and several of the topsheets 302 are provided in the form of a carrier web 318 which is cut along a first line 324 at a first end of the article length and along a second fine 325 along a second, opposite end of the article length.

In the alternative embodiment, pieces of reinforcement material 323, 323' are permanently attached in pairs to opposite edge portions of the carrier web 318 at an interval corresponding to the article length 316. A first web comprising several of the first belt halves 309 next to each other and a second web 320 comprising several of the second belt halves 309' next to each other are cut in order to provide one of the first 309 and one of the second 309' belt halves which, before cutting the carrier web 318, at one of their ends are permanently attached within bonding areas 313, 313' to the pieces of reinforcement material 323, 323' in order to provide the absorbent article with the belt 309, 309'.

In the alternative embodiment, the pieces of reinforcement material 323, 323' preferably are applied to extend outside the article width 317. This facilitates the fitting of an ultrasonic horn or another bonding unit which is to attach the belt ends to the pieces of reinforcement material.

As mentioned above, an elastic material advantageously is utilized in the pieces of reinforcement material 323, 323'.

In a method according to the invention, preferably the first 119; 219;319 and/or second 120; 220; 320 web comprise(s) portions of hook material 115; 215; 315 intended to be included in a hook-and-loop fastening system.

The above-mentioned bonding areas 113, 113'; 213, 213'; 313, 313' are advantageously created by means of thermal bonding with heat, or preferably with ultrasonics, though they can also be created by means of gluing.

In a method according to the invention, preferably two belt halves are simultaneously permanently attached to the carrier web 118; 218; 318, either directly or via the pieces of reinforcement material 323, 323'. This reduces the number of process stages and results in more efficient production.

As evident from the foregoing, the method according to the invention can be performed by means of a diaper machine or corresponding machine for transversal production or, alternatively, by means of a machine for longitudinal production. Such machines are commercially available, and it should not pose any difficulties to the skilled person having knowledge about the present invention to adapt such a machine in order to be able to implement the invention. Accordingly, it is not necessary to describe the basic technique and necessary equipment for manufacturing diapers herein.

In the foregoing, the present invention has been described by means of several embodiments and with reference to the attached drawings. However, the invention is by no means restricted to the specific embodiments which have been described above or shown in the drawings; instead the scope of the invention is defined by the following claims and equivalents thereof.

The invention claimed is:

1. An absorbent article comprising a liquid-pervious topsheet, a substantially liquid-impermeable backsheet and an absorbent body enclosed therebetween, said article having a front portion, a back portion and a crotch portion therebetween, and further being provided with a belt wherein the belt and the topsheet constitute separate members, the belt attached to the back portion of the article and adapted to be attached to the front portion of the article in such a way that the article assumes a pant shape, where the belt forms part of the waist portion of the pant and the belt has an outside surface and an inside surface, the inside surface being adapted to be in direct contact with a user, the belt comprises first and second belt halves which at one end of each half, a portion of the inside surface is permanently attached to the topsheet within bonding areas in such a way that the portion of the outside surface disposed within the bonding area is spaced farther from the backsheet than is the portion of the inside surface, and that each of said belt halves remains substantially flat along the entire length thereof when being brought against said topsheet on top of each other, and each of the belt halves has an uninterrupted portion extending from the respective bonding area in such a way that joints which are formed at said bonding areas will be at a position outside of the uninterrupted portion of the belt away from said user when the absorbent article is used;

said belt halves being fastened to each other during use to secure the absorbent article around the waist of the user.

2. The absorbent article according to claim 1, wherein pieces of reinforcement material are permanently attached to opposite edge portions of said topsheet, and that the inside surfaces of one end of said belt halves within the bonding areas are attached to said topsheet via said pieces of reinforcement material.

3. The absorbent article according to claim 1, wherein the article is a diaper or an incontinence guard.

4. The absorbent article according to claim 1, wherein one of the belt halves includes an attachment element for attaching an inside surface of the one belt half to an outside surface of the other belt half.

5. The absorbent article according to claim 1, further comprising fastening members attached to the front portion in such a manner that the fastening members attach to the outside of the belt halves when the belt halves are fastened to each other.

6. An absorbent article comprising a liquid-pervious topsheet, a substantially liquid-impermeable backsheet and an absorbent body enclosed therebetween, said article having a front portion, a back portion and a crotch portion therebetween, and further being provided with a belt wherein the belt and the topsheet constitute separate members, the belt attached to the back portion of the article and adapted to be attached to the front portion of the article in such a way that the article assumes a pant shape, where the belt forms part of the waist portion of the pant and the belt has an outside surface and an inside surface, the inside surface being adapted to be in direct contact with a user, the belt comprises first and second belt halves which at one end of each half, a portion of the inside surface is permanently attached to the topsheet within bonding areas in such a way that the portion of the outside surface disposed within the bonding area is spaced farther from the backsheet than is the portion of the inside surface, and that each of said belt halves remains substantially flat along the entire length thereof when being brought against said topsheet on top of each other, and each of the belt halves has an uninterrupted portion extending from the respective bonding area in such a way that joints which are formed at said bonding areas will be at a position outside of the uninterrupted portion of the belt away from said user when the absorbent article is used;

wherein pieces of reinforcement material are permanently attached to opposite edge portions of said topsheet, and that the inside surfaces of one end of said belt halves within the bonding areas are attached to said topsheet via said pieces of reinforcement material;

wherein the pieces of reinforcement material comprise an elastic material.

7. The absorbent article according to claim 6, further comprising fastening members attached to the front portion in such a manner that the fastening members attach to the outside of the belt halves when the belt halves are fastened to each other.

8. An absorbent article comprising a liquid-pervious topsheet, a substantially liquid-impermeable backsheet and an absorbent body enclosed therebetween, said article having a front portion, a back portion and a crotch portion therebetween, and further being provided with a belt wherein the belt and the topsheet constitute separate members, the belt attached to the back portion of the article and adapted to be attached to the front portion of the article in such a way that the article assumes a pant shape, where the belt forms part of the waist portion of the pant and the belt has an outside surface and an inside surface, the inside surface being adapted to be in direct contact with a user, the belt comprises first and second belt halves which at one end of each half, a portion of the inside surface is permanently attached to the topsheet within bonding areas in such a way that the portion of the outside surface disposed within the bonding area is spaced farther from the backsheet than is the portion of the inside surface, and that each of said belt halves remains substantially flat along the entire length thereof when being brought against said topsheet on top of each other, and each of the belt halves has an uninterrupted portion extending from the respective bonding area in such a way that joints which are formed at said bonding areas will be at a position outside of the uninterrupted portion of the belt away from said user when the absorbent article is used;

wherein a hook member of a hook-and-loop fastening means is provided on one of said inside surfaces of said belt halves, wherein the outside of the other belt half provides a loop material.

9. The absorbent article according to claim 8, further comprising fastening members attached to the front portion in such a manner that the fastening members attach to the outside of the belt halves when the belt halves are fastened to each other.

10. An absorbent article comprising a liquid-pervious topsheet, a substantially liquid-impermeable backsheet and an absorbent body enclosed therebetween, said article having a front portion, a back portion and a crotch portion therebetween, and further being provided with a belt wherein the belt and the topsheet constitute separate members, the belt attached to the back portion of the article and adapted to be attached to the front portion of the article in such a way that the article assumes a pant shape, where the belt forms part of the waist portion of the pant and the belt has an outside surface and an inside surface, the inside surface being adapted to be in direct contact with a user, the belt comprises first and second belt halves which at one end of each half, a portion of the inside surface is permanently attached to the topsheet within bonding areas in such a way that the portion of the outside surface disposed within the bonding area is spaced farther from the backsheet than is the portion of the inside surface, and that each of said belt halves remains substantially flat along the entire length thereof when being brought against said topsheet on top of each other, and each of the belt halves has an uninterrupted portion extending from the respective bonding area in such a way that joints which are formed at said bonding areas will be at a position outside of the uninterrupted portion of the belt away from said user when the absorbent article is used;

wherein a hook member of a hook-and-loop fastening means is provided on the outside surface of one of the belt halves, wherein the inside surface of the other belt half provides a loop material.

11. The absorbent article according to claim 10, further comprising fastening members attached to the front portion in such a manner that the fastening members attach to the outside of the belt halves when the belt halves are fastened to each other.

* * * * *